United States Patent [19]

Philippot et al.

[11] Patent Number: 4,792,331
[45] Date of Patent: Dec. 20, 1988

[54] DEVICE FOR OBTAINING AND ADMINISTERING UNILAMELLAR LIPOSOMES

[75] Inventors: Jean Philippot, St Clement La Riviere; Jean-Pierre Liautard, Montpellier, both of France

[73] Assignees: Centre National de la Recherche Scientifique; Institut National de la Sante et de la Recherche Medicale, both of Paris, France

[21] Appl. No.: 742,467
[22] PCT Filed: Oct. 5, 1984
[86] PCT No.: PCT/FR84/00221
   § 371 Date: Jun. 6, 1985
   § 102(e) Date: Jun. 6, 1985
[87] PCT Pub. No.: WO85/01440
   PCT Pub. Date: Apr. 11, 1985

[30] Foreign Application Priority Data

Oct. 6, 1983 [FR] France .................................. 83 16239

[51] Int. Cl.$^4$ .......................................... A61M 5/00
[52] U.S. Cl. ................................... 604/187; 604/190; 264/4.6; 424/450; 428/402.2; 436/829
[58] Field of Search ............... 264/4.6; 428/402.2; 424/38, 450; 436/829; 604/51, 84, 187, 190, 218

[56] References Cited

FOREIGN PATENT DOCUMENTS 0032578  7/1981  European Pat. Off. .
0056781  7/1982  European Pat. Off. .
2441385  6/1980  France .
2446635  8/1980  France .
8103280 11/1981  PCT Int'l Appl. .

OTHER PUBLICATIONS

Rhoden et al.: "Formation of Unilamellar Lipid Vesicles of Controllable Dimensions by Detergent Dialysis", Biochemistry, vol. 18, No. 19, 1979, pp. 4173–4178.

Roseveat et al.: "Alkyl Glycoside Detergents: A Simpler Synthesis and Their Effects on Kinetic and Physical Properties of Cytochromec Oxidase", Biochemistry, vol. 19, No. 17, 1980, pp. 4108–4115.

Mimms et al.: "Phospholipid Vesicle Formation and Transmembrane Protein Incorporation Using Octyl Glycoside", Biochemistry, vol. 20, No. 4, 1981, pp. 833–840.

Chem. Abstr., vol. 95, No. 9, Aug. 31, 1981, p. 393, 76456k.

Chem Abstr., vol. 97, No. 5, Aug. 2, 1982, p. 216, 35020m.

Chem. Abstr., vol. 98, No. 1, Jan. 3, 1983, p. 227, 2483g.

Chem. Abstr., vol. 99, No. 25, Dec. 19, 1983, p. 354, 209201e.

Fry et al., "Rapid Separation of Low Molecular Weight Solutes from Liposomes without Dilution", Analytical Biochemistry, 90, 809–815 (1978).

Szoka, Jr. et al.: "Procedure for Preparation of Liposomes with Large Internal Aqueous Space . . . ", Proc. Natl. Acad. Sci. U.S.A., vol. 75, No. 9, pp. 4194–4198, Sep. 1978.

Primary Examiner—Richard D. Lovering
Attorney, Agent, or Firm—Browdy and Neimark

[57] ABSTRACT

A device for obtaining unilamellar liposomes comprising means for forming a solution of lipids, a detergent (octylglucoside) and a pharmaceutically active substance; means for taking an aliquot quantity of said solution; permeable and/or semipermeable membrane partitions for eliminating said detergent by dialysis with polymers in the form of beads; and means for administering to patients the resulting solution free of detergent.

1 Claim, 1 Drawing Sheet

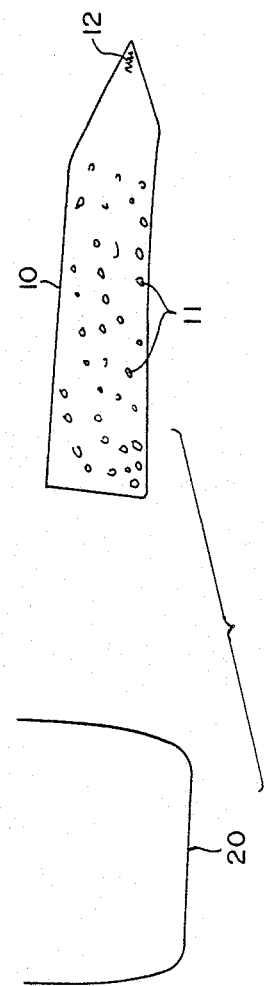

DEVICE FOR OBTAINING AND ADMINISTERING UNILAMELLAR LIPOSOMES

FIELD OF THE INVENTION

This invention relates to an improved process for obtaining unilamella liposomes of high diameters and pharmacological application thereof for encapsulating an active principle for extemporaneous administration thereof.

BACKGROUND OF THE INVENTION

During the last few years, many studies have shown that liposomes can be used for encapsulation and transfer of an active substance into cells. To this end, phospholipid vesicles have been mainly prepared by physical techniques such as ultra-sounds, the so called "French press" technique or chemical procedures by using organic solvents or detergents followed by elimination of the latter.

However, the liposomes obtained nowadays present either structures or dimensions which do not always permit either encapsulation of certain macromolecules of a cumbersome nature or encapsulation of a relatively high quantity of active substance, with encapsulated quantities remaining until now limited to certain values.

SUMMARY OF THE INVENTION

Consequently, the purpose to reached by the Applicants is to find out a process for preparation of big unilamellar liposomes capable of encapsulating macromolecules of high dimensions (proteins or nucleic acids), on the one hand, and on the other hand, of encapsulating higher quantities of an active substance than was possible until now. Furthermore, such process should be sufficiently moderate and more especially should avoid contact with a an organic solvent, denaturing proteins or high energies such as ultra-sonic emission or the application of pressures capable of breaking up molecules of nucleic acids. The procedure having recourse to detergent appears to be the best method of preserving the structure and activity of such macromolecules.

Elimination of the detergent by dialysis or the filtration method on gel provides unilamellar liposomes. The internal volume of such liposomes varies with the nature of the detergent, the molecular ratio of the detergent to phospholipids, the lipid composition of the vesicles and the dialysis rate. The vesicle dimensions appear to be different in size but in the same order of magnitude whether it be after dialysis or after filtration on gel. However, scarceness and/or costs of the molecules to be encapsulated (antibodies, enzymes, purified or ARN carrier genes) require very high encapsulation rate and exclude procedures requiring large quantities of substance to be encapsulated as well as elimination of the detergent through filtration on gel.

The process according to the invention is based on the procedure of elimination of the detergent by dialysis and is an improvement thereof. As a matter of fact, one of the main disadvantages encountered upon formation of liposomes by the procedure utilizing detergents resides in that elimination of the detergents is never total; very often a significant quantity of detergent remains even after exhaustive dialysis. Thus, with the usually employed detergents, in particular, sodium cholate or desoxycholate and "Triton X-100", the residual quantity can be from a few % to 10%.

The Applicants however found in an entirely unexpected manner that if the detergent used for lipid solubilization for the formation of a liposome is a neutral detergent presenting a high critical micellar concentration under certain dialysis conditions, its quick and almost total elimination can be obtained thereby to permit realization of liposomes encapsulating an active principle such as a medicament practically free of detergent.

Furthermore, unilamella liposomes of high diameter from 200 to 1000 nm are obtained, which are therefore capable of encapsulating either large molecules in suitable quantities or high quantities of less cumbersome molecules thereby to remedy the disadvantages inherent to the known liposomes.

The Applicants have noted that for the particular application as the vehicle of a medicament practically free of detergent there can be cited as a detergent responding to the above definition, suitable according to the invention, octylglucoside which also presents the property of being compatible with a large quantity of the active substances that would be encapsulated.

According to another characteristic of the invention, a ratio of detergent to lipids of 10:1 to 12:1 is preferably used.

According to still another characteristic, elimination of the detergent is effected by means of synthetic polymers advantageously in form of beads selected preferably from the group comprising synthetic polymers of a high adsorbing power of the styrene-divinylbenzene type, disposed in the dilution medium.

Finally, according to another characteristic, the lower the ratio of detergent to beads (micromole/mg), the more total and rapid the elimination of the detergent.

The invention also covers the above mentioned process as applied to encapsulation of an active substance characterized by adding the substance to be encapsulated to the desired lipids solubilized in the detergent according to the invention and eliminating said detergent by means of said high adsorbing power synthetic polymers.

It also covers extemporaneous preparation of a medicament consisting of taking the desired volume of a mixture of the mixed solution of lipids, detergent and the substance to be encapsulated, proceeding with elimination of the detergent advantageously after direct contact with the beads, then injecting the liposome free of detergent to the patient.

DESCRIPTION OF THE INVENTION

According to an advantageous mode of embodiment, it is proceeded at the time of use by means of a sampling syringe loaded with the agent adsorbing the detergent, and provided with a suitable filter or sieve, at its base.

Further advantages and characteristics of the invention will appear more clearly from the following description.

As previously mentioned one of the main difficulties encountered upon formation of the liposomes by the procedure having recourse to a solubilizing detergent resides in that a non negligible residual quantity of detergent subsists in the obtained liposomes even after preceeding, for elimination of said detergent, with an elaborate dialysis operation (a few percentages in the case of sodium cholate or desoxycholate and about 10% in the case of "Triton X-100"). However, if for example octylglucoside is selected as the detergent, it is noted that it can be eliminated almost completely (residual quantity lower than 0.05%) and quickly. This unexpected and unforeseeable result is attributed, and this constitutes the base and the interest of the invention, to the fact that such detergent presents very high micellar concentration which facilitates quick rejection thereof from mixed micellar complexes. It has also been noted almost generally that a molar ratio of such detergent to the lipid comprised between 10:1 and 12:1 was suitable to obtain a limpid lipid solution. It is to be noted that the presence of cholesterol does not modify the solubilization degree of lipid mixtures.

As regards elimination of such detergent, one has used dialysis and an adsorbing polymer of high porosity advantageously in form of beads, such polymer being selected preferably from those formed from styrene-divinylbenzene of the "Amberlite X AD-2" type marketed by the firm BIO RAD under the name of "Bio Beads SM2".

Experiments realized with this type of beads but with a detergent which is, apart from octylglucoside, "Triton X-100" and sodium desoxycholate, show that adsorption of the detergent and therefore of octylglucoside depends on the ratio of detergent to beads. Moreover, as compared to the corresponding adsorption of "Triton X-100" it is noted that octylglucoside is fixed more quickly to these balls than "Triton X-100". Moreover, it is observed that there is an optimum ratio of detergent to beads beyond which elimination of the detergent is no longer improved. This optimum ratio is 0.11 for octylglucoside (1 micromole of detergent/9 mg of beads) and it corresponds to total rejection of the detergent from the medium, whereas this same optimum ratio is 0.05 in case of "Triton X-100" (1 micromole of detergent/20 mg of beads) with a residual quantity of detergent of 0.25%, such quantity not being reducible by adding a supplementary quantity of beads (29 mg of beads/micromole of detergent). This confirms what is known by any man of the art, i.e. the difficulty of eliminating "Triton X-100" from such media. However, this also shows the high improvement realized when the means offered by the invention are used.

Another series of tests also permitted to appreciate the connectibility of said beads to the phospholipids during a typical preparation of liposomes by using direct contact between mixed detergent and phospholipid micelles and beads such as defined above, and to also compare the effects of "Triton X-100" and octylglucoside upon such phenomenon. To this end, an identical quantity of lipids (molar ratio PC/PS of 1:1-PC designating phosphatidylcholine and PS phosphatidylserine) was solubilized by means of such detergents with a molar ratio of detergent to phospholipids of 8, then samples of these media were mixed with said beads and the concentrations of the solutions were determined by a kinetic analysis. Under these conditions, liposomes could be obtained in a very short period of time. However, it must be noted that a large quantity of lipids appears to be fixed to the beads in both cases. In fact, this is only a dilution resulting from the liquid volume emprisoned by beads. Therefore, there is no loss of lipid by fixation.

In any case it is observed that beyond a threshold of concentration in beads such total and rapid elimination of the detergent is obtained whatever be the quantity of beads used. The lower the ratio of detergent to beads (micromole/mg), the quicker is however such elimination. Moreover, the quantity of lipid present in the mixture (such as can be determined by means of $^{14}C$-PC) appears to decrease as the quantity of beads in the medium (dilution of the lipids by the internal volume of the beads) increases.

Anyhow, these results emphasize the aptitude of beads considered to adsorb many different compounds whether their molecules be neutral or loaded. Such aptitude of polystyrene beads was not mentioned until now. However, such procedure implying direct contact with the beads may not be suitable for encapsulation of certain macromolecules.

However such media and such beads can advantageously be used for such encapsulation in accordance with this invention by proceeding through the dialysis technique.

Thus, for example, in the course of a series of tests it was proceeded with hydration of 20-30 micromoles of dried lipids, either by means of 0.125 ml of a fluorescent antibody buffered solution (1.25 mg of protein) or by means of a solution of tARN (400 microg/ml), then with solubilization thereof by means of octylglucoside by using a molar ratio of detergent to lipid of 10:1 in a final volume of 0.675 ml. It was proceeded with dialysis against 100 ml of a buffer solution containing different quantities of beads (0.04 to 0.1 micromole of detergent/mg of beads). The results obtained by such procedure were then compared with those obtained by the conventional dialysis by changing four times one volume of 1000 ml of buffer solution.

For a ratio of detergent to beads lower than 0.1, all detergent molecules are adsorbed in less than one hour by direct contact between detergent and beads. The same results are obtained 24 hours later when the beads are added to the dialysis medium. It is noted that such a ratio lower than 0.1 accelerates elimination of detergent. The comparative test thus shows that this procedure produces quicker detergent elimination with 100 ml only of buffer solution.

It has also been checked that such dialysis using these beads does not modify lipid concentration.

Furthermore, the diameters of the obtained vesicles were measured by electronic microscopy; it is determined that the liposomes in question present very homogeneous dimensional distribution.

DESCRIPTION OF THE DRAWING

FIG. 1 shows a device according to the present invention for obtaining unilamellar liposomes.

A syringe 10 contains polymer beads 11. A sieve 12 is provided at the base of the syringe. A means for mixing ingredients is shown at 20.

In use, a solution of lipids, active substance, and detergent is formed in means 20. This solution is then taken up by a syringe 10. The syringe contains polymeric beads 12 which absorb the detergent. A sieve 13 is provided at the base of the syringe just in front of the needle 14. The piston in relation to the syringe body is shown below the diagram of the syringe. After several minutes of stirring, it is possible to inject a patient with unilamellar liposomes free of any detergent directly from the syringe by transferring the liposomes through the sieve at the base of the syringe into the patient.

The following Example illustrates a type of liposome that can be obtained by carrying out the invention.

EXAMPLE

(1) Preparation of the lipid octylglucoside mixture

The lipids (stored at −30° C. in a mixture of chloroform and methanol of 2:1 (v/v) is mixed in different proportions and for the experimentation needs there is added as desired a suitable quantity of phosphatidylcholine [C14] as the tracing element. The solvent is evaporated by submitting the mixture (final concentration 10–30 mM) to a nitrogen stream, then under vacuum for one hour. Thereafter, the substance to be encapsulated is added thereto with a buffer solution (L) [10 mM Hepes (4-(2-hydroxyethyl)-piperazineethane-1-sulfonic acid) (pH=7.4)/1 mM EGTA/150 mM NaCl] and after stirring in Vortex the lipids are hydrated for 30 minutes at a temperature higher than the highest transition temperature of the constituents of the mixture. Then, the detergent (octylglucoside) is added with, if necessary, a suitable quantity of the same detergent, radioactive as tracer for the experimentation needs.

The suspension of the multilamellar liposomes is transformed to a limpid solution. Such mixture sealed under vacuum in a flask should be preservable for several months.

(2) Detergent elimination and unilamella liposome formation encapsulating the active substance

2.1. Elimination by dialysis:

The desired volume of the above mixed solution (lipid+active substance+detergent) is taken up and dialyzed against 100 ml of buffer containing a quantity of such beads as previously defined and in the optimum ratio. It is stirred for several hours; unilamella liposomes are formed, containing the added active substance encapsulated within them. Such liposomes are then ready for use.

The following Table illustrates some characteristics of liposome types obtained in accordance with the invention with elimination by dialysis,

| Properties | Composition of lipids | | |
|---|---|---|---|
| | PC | PC/PS (1:1) | PC/PS/Cholesterol (1:1:1) |
| Encapsulated protein % | 26 | 11 ± 2 | 47 ± 4 |
| Encapsulated ARN % | not determined | not determined | 45 ± 4 |
| Calculated diam.* (nm) | 540 | 237 ± 50 | 920 ± 100 |
| Diameter measured by electronic microscope (nm) | 300–500 | 100–240 | 600–1100 |
| Internal volume (l/mole PL) | 20 | 8 | 35 |

*The total encapsulated volume was calculated on the basis of a total area of 75 Å$^2$ per one molecule of phospholipid through the equation: % of encapsulation = 37 × M × d × 10$^2$ where M=phospholipid concentration (mol/liter) and
d=diameter (micrometers).

As can be seen from this Table, the liposome diameter varies in a large proportion with the lipid composition. The liposomes PC-PS have a diameter of 200 nm, whereas addition of cholesterol thereto gives vesicles with a diameter of 1000 nm. This cholesterol effect upon the dimensions of the vesicles is known.

Electronic microscope examination shows that such vesicles are unilamellar. This is confirmed by comparing the volume of the intravesicular compartment (given by the equation reminded above) with the volume that can be expected for unilamellar vesicles as measured by electronic microscopy in the same liposome preparation. The intravesicular compartment is measured by encapsulating either antibodies coupled to fluoresceine or ARN's; the diameter is deduced therefrom according to the known relationship between vesicular dimensions and the volume percentage of encapsulated substance in unilamellar vesicles.

The above Table establishes clear correspondence between the diameters obtained by both of these methods. Thus, the liposomes according to the invention are mainly unilamellar.

Moreover, such liposomes contain a very high quantity of encapsulated substance i.e. 35 l/mole of lipid in case of PC-PS-cholesterol liposomes. Such quantity is much higher than that which can be obtained for example by evaporation with phase reversal which would be of 10 l/mole of lipid. Moreover, a reasonable quantity of lipid (13 mM) permits incorporation of a proportion of up to 50% of macromolecules which can be compared to the results that can be obtained in case of phase reversal.

Furthermore, in view of the high potential produced in small, loaded liposomes, encapsulation of molecules carrying the same load is reduced. This eliminates the possibility of using small liposomes containing PS's to encapsulate nucleic acids. However, the liposomes according to the invention avoid such constraint and permit the same encapsulation rate both for ARN's and IgG's which are slightly positive proteins.

Thus, the liposomes according to the invention present all the desired properties for transfer of macromolecules to cell cultures. Big vesicles are more efficient for works implying transfer of macromolecules to cells due to the fact that they can encapsulate a greater quantity of substance for the same mass of lipids. Thus, for example, a liposome of 100 nm carries 3.10$^7$ molecules when it is loaded with a solution 1M. Due to this, capture of one liposome per cell appears to cover most cases. Moreover, the lipid composition (PC-PS-cholesterol) is not toxic in respect to many cells and even permits fusion with cellular membranes under conditions known to favour this phenomenon such as for example the use of poly(ethyleneglycol). In this case, the unilamellar liposomes of the invention makes this procedure easier.

IgG's and ARN's are not denatured and keep all activity after encapsulation thereof. The high incorporation rate (up to 50% for 13 mM of phospholipid) makes the invention very suitable for encapsulation of macromolecules which are normally difficult to obtain in large quantities such as RNA, monoclonated antibodies and monoclonated ADN.

2.2. Extemporaneous preparation

A very interesting application derived from such property consists of preparing and administering extemporaneously a medicament to a patient by directly mixing the mixed solution (lipid+active substance+detergent) to the beads. To this end, it is proceeded in the following manner: After obtaining the mixed solution of lipids, detergent and the substance to be administered as described above, it is proceeded with the taking up of such solution by means of a syringe provided at its base with a sieve and containing beads such as previously defined. After several minutes of stirring, it is possible to inject with the same syringe the unilamellar liposomes free of any detergent and containing the active substance resulting from this operation in accordance with the invention, with an encapsulation rate compatible with the lipid quantity used.

It will be understood that this invention was only described in a purely explanatory and not at all limitative manner and that any useful modification can be made thereto without however departing from its scope.

We claim:

1. A device for obtaining unilamellar liposomes comprising:
   means for forming a solution of lipids, a detergent selected from the group consisting of octylglucosides, and a pharmaceutically active substance;
   means for taking an aliquot quantity of said solution;
   permeable and/or semipermeable membrane partitions for eliminating said detergent by dialysis with polymers in the form of beads; and
   means for administering to patients the resulting solution free of detergent.

* * * * *